US00PP18646P3

(12) United States Plant Patent

Hambuchen et al.

(10) Patent No.: US PP18,646 P3
(45) Date of Patent: Mar. 25, 2008

(54) *LAGERSTROEMIA INDICA* 'ORCHID CASCADE', COMMONLY KNOWN AS CREPEMYRTLE

(50) Latin Name: *Lagerstroemia indica*
Varietal Denomination: Orchard Cascade commonly known as Crepemyrtle

(76) Inventors: Robert E. Hambuchen, 3040 Dallas Loop, Conway, AR (US) 72034; Betty Hambuchen, 3040 Dallas Loop, Conway, AR (US) 72034

( * ) Notice: Subject to any disclaimer, the term of this patent is extended or adjusted under 35 U.S.C. 154(b) by 48 days.

(21) Appl. No.: 11/217,785

(22) Filed: Sep. 1, 2005

(65) Prior Publication Data

US 2007/0056065 P1 Mar. 8, 2007

(51) Int. Cl.
*A01H 5/00* (2006.01)

(52) U.S. Cl. ..... Plt./252

(58) Field of Classification Search ..... Plt./252
See application file for complete search history.

*Primary Examiner*—Anne Marie Grunberg
*Assistant Examiner*—Louanne Krawczewicz Myers

(57) ABSTRACT

'Orchid Cascade' is a new and distinct variety of *Lagerstroemia indica,* commonly referred to as Crepemyrtle. It is a low growing variety where the primary limbs arch and cascade out and downward. It has a height of 16 to 24 inches at maturity with substantially no upward growth. It can reach a width of 40 to 48 inches. This cultivar is an early blooming variety which starts to bloom in early June and is normally in full bloom in plant zone 7B by mid June. It appears to be multi-colored blooming crepemyrtle because of the fading habit of some of its blooms. This color appears to range from a deep lavender/pink to an almost white in appearance with several shades in between. The cultivar is cold hardy to 10 degrees Fahrenheit and is very highly resistant to powdery mildew.

3 Drawing Sheets

Latin name of genus and species of the plant claimed: *Lagerstroemia indica.*

Variety denomination: *Lagerstroemia indicia* 'Orchid Cascade', commonly known as Crepemyrtle.

BACKGROUND OF THE INVENTION

1. Field of the Invention

The present invention relates to a new and a distinct variety of landscape plant *Lagerstroemia indica* 'Orchid Cascade'.

2. Description of Prior Art including Information Disclosed Under 37 CFR 1.97 and 1.99

This new and afore mentioned cultivar 'Orchid Cascade' was found growing in a bed of rooted cuttings in our growing facility in Conway, Ark. all made from the same low-growing and spreading but unnamed seedling *Lagerstroemia indica.* This new cultivar has a cascading growth pattern, is more compact and has a different leaf color and leaf arrangement than the original parent plant. Its bloom is more profuse and has its own distinctive color pattern. This new plant has been asexually reproduced using both hardwood and softwood cuttings in our rooting facilities in Conway, Ark. The new variety is stable and reproduces true-to-type in successive generations of asexual reproduction.

SUMMARY OF INVENTION

This invention involves the discovery of a new and a distinct variety of *Lagerstroemia indica* which has been given the name 'Orchid Cascade'. This new cultivar is characterized by a vigorous, low growing, spreading and cascading growth pattern. The plant reaches a height of 16 to 24 inches at maturity in a cascading growth pattern with substantially no vertical growth. As new primary limbs appear and grow, secondary limbs appear. Sometimes we see 12 to 14 secondary limbs on the primaries. As the plant blooms there are inflorescences at the terminal ends of both primary and secondary limbs and often there are double inflorescences on both the primary and the secondary limbs. This produces a foam of color over the entire plant. Flower buds open with an orchid or lavender/pink color bloom. Shortly after opening, some of the blooms fade to an almost white color long before they drop. This creates the appearance of a multi-color flowering crepemyrtle. We should also note that later in the bloom period we occasionally see a new bud open with a very light color, almost white flower bloom. The stamens are a yellow color. 'Orchid Cascade' is an early blooming cultivar with flowers opening in early June and is in full color by mid-June in Central Arkansas, plant zone 7b. Plants continue to produce blooms into late October. Only a few seed pods develop in the early bloom season, usually only 3 to 5 per inflorescence. This increases with each round of blooms so that the late inflorescence will develop from 17 to 20 seed pods. These seed pods are globate in form or shape. They range in size measuring 1.4 to 1.5 centimeters in length and having a width of 0.8 to 0.9 centimeters. Each pod can contain from 14 to 25 seeds which are winged. The actual seeds, with the wing removed are a 0.1 to a 0.15 centimeter in diameter and 0.25 to 0.3 centimeters in length. Their shape, with the wing attached, is unique much like a very small and thin segment of an orange. The color of matured and dried seeds is predominantly a gray orange, R.H.S. 174B.

DETAILED BOTANICAL DESCRIPTION

Figure 1:
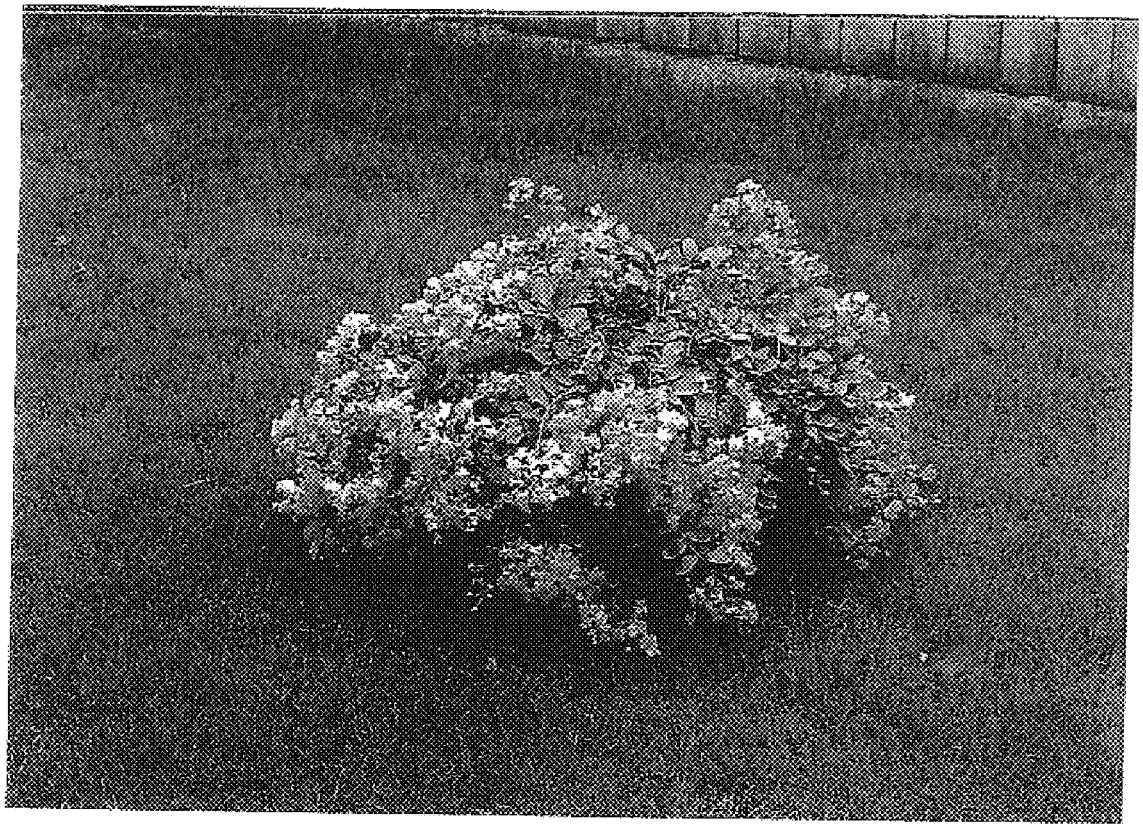
FIG. 1 is a photographic view of an early blooming 3 year old cultivar in a 5 gallon container.
Figure 2:
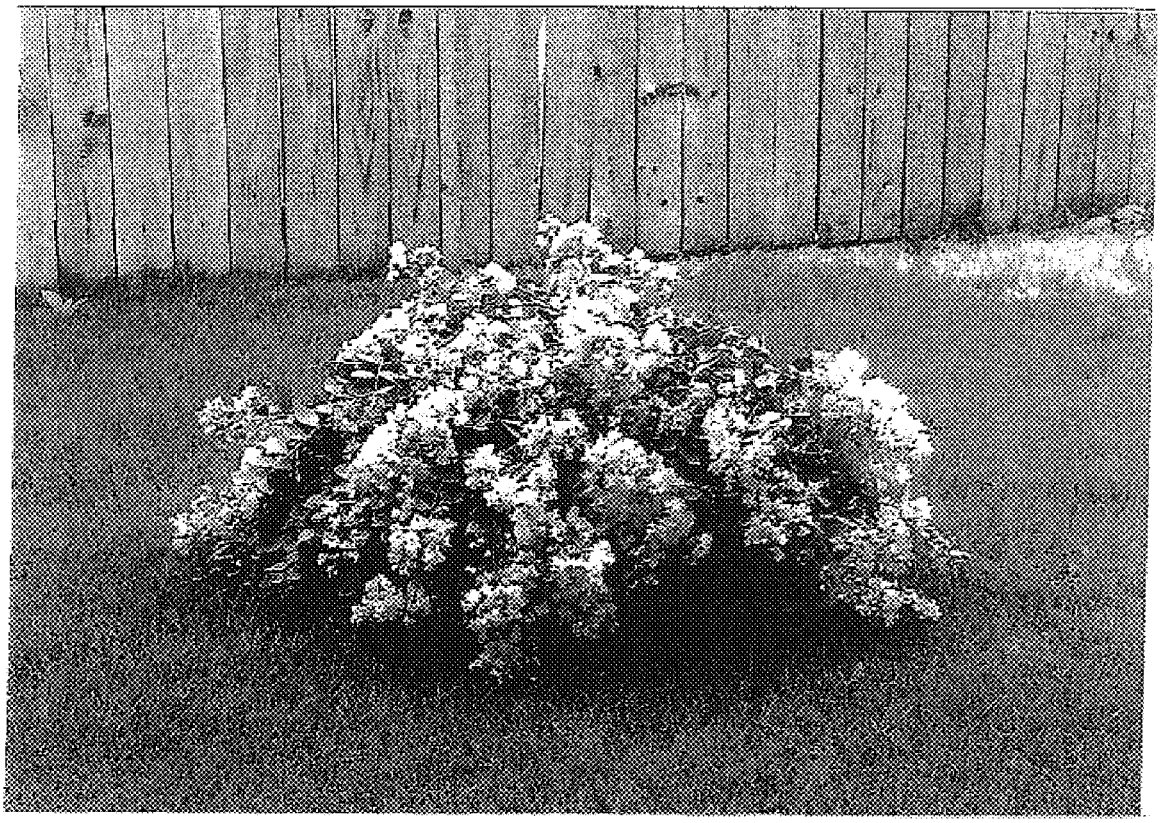
FIG. 2 is a photographic view of the multi color appearance of the 3 year old cultivar while growing in a 5 gallon container.
Figure 3:
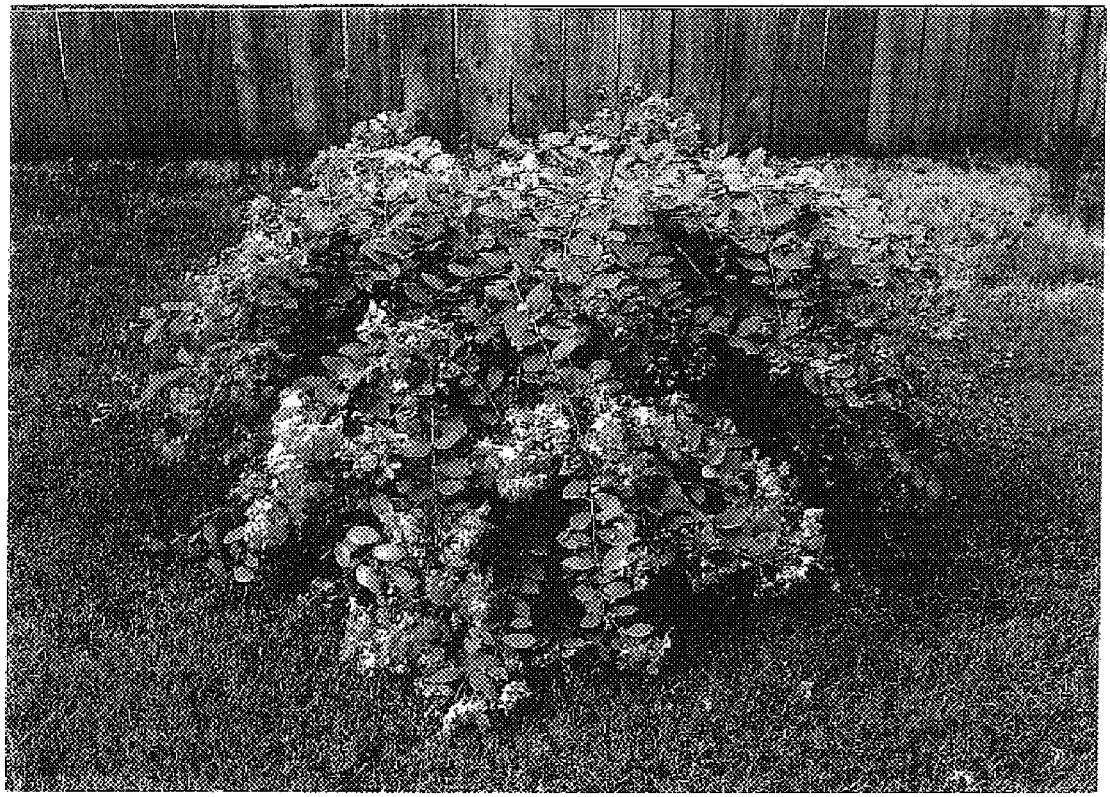
FIG. 3 is a photographic view of a 4 year old cultivar 'Orchid Cascade' in a 7 gallon container displaying the arching and cascading growth habit, along with its low-growing potential.

The plants described were grown in an outdoor cultivated nursery bed located in Conway, Ark. The age of the plants was approximately 3 to 4 years old. Observations and measurements were mainly taken during flowering. A detailed description of the new variety follows and the terminology adapted by The Royal Horticultural Society Colour Chart (R.H.S.) has been followed.

Classification:

*Botanical.*—*Lagerstroemia indica.*

*Commercial.*—Crepemyrtle cv. 'Orchid Cascade'.

Parentage: The selected plant was found growing in a bed of rooted cuttings made from the same low-growing and spreading but unnamed seedling *Lagerstroemia indica.* The selected plant was named 'Orchid Cascade' and was asexually propagated by both hardwood and softwood cuttings. The new variety is stable and reproduces true in successive generations of asexual reproduction.

Growth: The plant is a low growing and compact cultivar with arching and cascading limbs. At maturity, the plant will grow to a height ranging from 16 to 24 inches. It can reach a width of 40 to 48 inches. The cultivar is cold hardy, withstanding temperatures of 10 degrees Fahrenheit with no visible damage or delay in the early bloom period. The cultivar has a very high resistance to powdery mildew.

Branches: The branches of this plant consist of 6 to 12 primary branches measuring 40 to 60 cm in length. The branch height ranges from 7 to 9 centimeters above the soil line. The primary limbs on a fully mature plant (3 to 4 years) will grow to a diameter of 0.8 to 1 centimeter. Many of the primary limbs produce a number of secondary limbs in an alternate position along the entire length. The length of these secondary limbs varies greatly and range from 12 to 36 centimeters. It is common to see as many as 12 to 14 secondary limbs on each primary limb. Often this gives the primary limbs a fan like appearance. Mature limbs maintain their cascading form and appearance. The diameter of the secondary limbs ranges from 0.2 to 0.35 centimeters. Internodes occur about 4.5 to 5.0 centimeters along each side of the primary limbs. And in like manner, internodes occur 2.3 to 2.5 centimeters on the secondary limbs. New branches, exposed to the sun, are a red purple, R.H.S. 59B on side exposed to sun, and a green yellow, R.H.S. 145C on the non exposed side. As the limbs mature the color changes to a grey green, R.H.S. 197B.

Foliage: Leaf arrangement for the entire plant is primarily alternate with an occasionally opposite arrangement. The leaf type for both young and mature leaves is simple with pinnate venation and an entire margin with no serrations. Leaf texture on young and mature leaves is smooth on both the adaxial and abaxial sides. Vein color in young leaves is red purple, R.H.S. 60C on both the adaxial and abaxial sides. As the leaf matures the vein color changes to a yellow green, R.H.S. 148C on both the adaxial and abaxial sides. Leaves are ellipse or ovate with an acute tip and base. Mature leaf size varies greatly ranging from a length of 2.5 to 7.0 centimeters and a width of 1.2 to 3.6 centimeters. Mature leaf color is green, R.H.S. 137A and on the adaxial side and green, R.H.S. 137D on the abaxial side. Young leaves contain a red purple, R.H.S. 60C margin on both sides. As the leaf matures, the red purple margin color fades. The leaf petiole is less than 1 millimeter in length and less than 1 millimeter in diameter. Petiole color yellow green, R.H.S. 148C.

Flower: Flower bud is globate in shape with smooth texture. Flower buds are located on the terminal portion of most lateral branches and usually produce 8 to 23 flower buds per branch. Extensive branching leads to numerous inflorescences per plant. Inflorescences develop at the terminal end of each branch, with many inflorescences forming doublets. Single inflorescences measure 9 to 11 centimeters in length and 7 to 9 centimeters in diameter on both the primary and secondary limbs. Double inflorescences range from 8 to 9 centimeters in length and 7 to 8 centimeters in diameter. Each inflorescence may contain 12 to 30 individual blooms. Bloom buds range from 0.7 to 0.9 centimeters in width to 0.8 to 1.0 centimeters in length and have 6 or 7 sepals per bud. Sepals are 0.3 to 0.4 centimeters in width and 1.2 to 1.4 centimeters in length are lobed shaped with an acute tip and base. The margin on the sepal is complete. Sepals have a red purple color, R.H.S 60C near the base which transitions into a green R.H.S. 137D near the apex. This color formation is similar on both sides of the sepal. Blooms initiate in early June to mid June in zone 7B. Blooms continue into late October.

Blossom: Petals shape is distinct forming a crumpled oval with the entire margin serrated. The apex of the petal comprised the crumbled oval with the base attaching to inside portion of the flower base. The filament is approximately 1 centimeter in length and is violet R.H.S. 84B. Six petals comprise the blossom. Average petal length is approximately 1.7 centimeters and approximately 1.5 in width. An individual blossom will last approximately 10 days on the plant. The blossom, on both sides is initially violet R.H.S. 84A, transitioning to violet R.H.S. 84B, violet R.H.S. 84C and subsequently to violet R.H.S. 84D before the blooms fall. Occasionally a blossom will bloom as a light violet, R.H.S. 84D and not proceed through a color transition. Both sides of the flower blossom adhere to this color pattern. No fragrance is noted for this variety.

Reproductive organs: Stamens are formed in two whorls with one of the filaments longer than the other. Filaments are light yellow, R.H.S. 8D, with anthers and pollen being a yellow orange, R.H.S. 15B. A single pistil is present, with the style a light green color, R.H.S. 138A, and the stigma shown as a red purple color, R.H.S. 60B. The flower is perigynous with a superior ovary containing many ovules. The brown fruit, R.H.S. 200B, is round with a hard dry covering and globate in shape. The seed pods or fruit range in size from 1.4 to 1.5 centimeters in length and 0.8 to 0.9 centimeters in width. Each pod may contain approximately 14 to 25 seeds. The actual seeds, with the wing removed are a 0.1 to a 0.15 centimeter in diameter and 0.25 to 0.3 centimeters in length. Their shape, with the wing attached, is unique much like a very small and thin segment of an orange. The color of matured and dried seeds is predominantly a gray orange R.H.S. 174B. Each plant may produce several hundred seeds, but because the plant is semi-sterile, few seeds are viable.

We claim:

1. A new and distinct variety of crepemyrtle plant substantially as shown and described characterized by low growing, yet extensive cascading lateral branching that reaches a height of 16 to 24 inches with substantially no upward growth, it is early blooming, profuse and has distinctive lavender pink inflorescences that tend to fade to a lighter color as they mature and it has very high resistance to powdery mildew.

* * * * *